US011060084B2

(12) United States Patent
Saksela

(10) Patent No.: US 11,060,084 B2
(45) Date of Patent: Jul. 13, 2021

(54) SH3 DOMAIN DERIVATIVES

(71) Applicant: Next Biomed Therapies Oy, Helsinki (FI)

(72) Inventor: Kalle Saksela, Espoo (FI)

(73) Assignee: Next Biomed Therapies Oy, Helsinki (FI)

( * ) Notice: Subject to any disclaimer, the term of this patent is extended or adjusted under 35 U.S.C. 154(b) by 754 days.

(21) Appl. No.: 15/742,934

(22) PCT Filed: Jul. 8, 2016

(86) PCT No.: PCT/FI2016/050509
§ 371 (c)(1),
(2) Date: Jan. 9, 2018

(87) PCT Pub. No.: WO2017/009533
PCT Pub. Date: Jan. 19, 2017

(65) Prior Publication Data
US 2018/0230456 A1    Aug. 16, 2018

(30) Foreign Application Priority Data
Jul. 10, 2015    (FI) .................................... 20155554

(51) Int. Cl.
*C12N 15/10*    (2006.01)
*C07K 14/47*    (2006.01)
*C12N 15/63*    (2006.01)

(52) U.S. Cl.
CPC .......... *C12N 15/1037* (2013.01); *C07K 14/47* (2013.01); *C12N 15/63* (2013.01)

(58) Field of Classification Search
CPC ................ C07K 14/47; C12N 15/1037; C12N 15/1092; C12N 15/62; C12N 15/63; C40B 40/02; C40B 40/10; G01N 33/6845
See application file for complete search history.

(56) References Cited

U.S. PATENT DOCUMENTS 6,309,820 B1 * 10/2001 Sparks ............... C12N 15/1037
506/9
2007/0212700 A1 * 9/2007 Ranganathan ......... G16B 30/00
435/6.16

FOREIGN PATENT DOCUMENTS

WO    WO-2008022759 A2 *    2/2008 .............. A61P 37/04

OTHER PUBLICATIONS

Nephrocystin-1 isoform X2 of Propithecus coquereli from the Protein NCBI database reference sequence XP_012497349.1 (Year: 2015).*

(Continued)

*Primary Examiner* — Jeremy C Flinders
(74) *Attorney, Agent, or Firm* — Laine IP Oy

(57) ABSTRACT

The present invention is directed to SH3 domain derivatives having a specific binding affinity to a target molecule. In this respect, the invention provides SH3 domain derivatives of nephrocystin (NPHP1) and the Tec kinase. The invention also provides a method for the production of a library comprising recombinant derivatives of NPHP1 or the Tec kinase SH3 domains and a method for selecting from the library one or more derivatives of the SH3 domain of nephrocystin (NPHP1) or the Tec kinase having a specific binding affinity to a target molecule.

11 Claims, 2 Drawing Sheets

Specification includes a Sequence Listing.

(56) References Cited

OTHER PUBLICATIONS

Amako et al: "Hepatitis C virus NS5A inhibits mixed lineage kinase 3 to block apoptosis." J Biol Chem 288, 2013, pp. 24753-24763.

Antoku et al: "A crucial role in cell spreading for the interaction of Abl PxxP motifs with Crk and Nck adaptors." J Cell Sci 121, 2008, pp. 3071-3082.

Asbach et al: "Comprehensive analysis of interactions between the Src-associated protein in mitosis of 68 kDa and the human Src-homology 3 proteome." PLoS One 7, 2012, e38540.

Binz et et al: "Engineered proteins as specific binding reagents." Current opinion in biotechnology 16, 2005, pp. 459-469.

Brack et al: "A bispecific HER2-targeting FynomAb with superior antitumor activity and novel mode of action." Molecular cancer therapeutics 13, 2014, pp. 2030-2039.

Gebauer et al: "Engineered protein scaffolds as next-generation antibody therapeutics." Current opinion in chemical biology 13, 2009, pp. 245-255.

Grabulovski et al: "A novel, non-immunogenic Fyn SH3-derived binding protein with tumor vascular targeting properties." J Biol Chem 282, 2007, pp. 3196-3204.

Heikkinen et al: "Avian and 1918 Spanish influenza a virus NS1 proteins bind to Crk/CrkL Src homology 3 domains to activate host cell signaling." J Biol Chem 283, 2008, pp. 5719-5727.

Hey et al: "Artificial, non-antibody binding proteins for pharmaceutical and industrial applications." Trends in biotechnology 23, 2005, pp. 514-522.

Hiipakka et al: "SH3 domains with high affinity and engineered ligand specificities targeted to HIV-1 Nef." J Mal Biol 293, 1999, pp. 1097-1106.

Hiipakka et al: "Versatile retargeting of SH3 domain binding by modification of non-conserved loop residues." FEBS Lett 581, 2007, pp. 1735-1741.

Járviluoma et al: "High-affinity target binding engineered via fusion of a single-domain antibody fragment with a ligand-tailored SH3 domain." PLoS One 7, 2012, e40331.

Kesti et al: Reciprocal regulation of SH3 and SH2 domain binding via tyrosine phosphorylation of a common site in CD3epsilon. J Immunol 179, 2007, pp. 878-885.

Kleine et al: "Preferred SH3 domain partners of ADAM metalloproteases include shared and ADAM-specific SH3 interactions." PLoS One 10, 2015, e0121301.

Kärkkáinen et al: "Identification of preferred protein interactions by phagedisplay of the human SRC homology-3 proteome" EMBO Rep 7 2006, pp. 186-191.

Igioi et al: "The hepatitis C virus NS5A protein blocks EGFR degradation via a praline motif dependent interaction." J Gen Viral, 2015.

Li: "Specificity and versatility of SH3 and other praline-recognition domains: structural basis and implications for cellular signal transduction." FEBS Lett 513, 2002, pp. 30-37.

Macias et al: "WW and SH3 domains, two different scaffolds to recognize praline-rich ligands." FEBS Lett 513. 2002, pp. 30-37.

Mayer: "SH3 domains: complexity in moderation." J Cell Sc. 114, 2001. pp. 1253-1263.

Neuvonen et al: "SH3 domain-mediated recruitment of host cell amphiphysins by alphavirus nsP3 promotes viral RNA replication." PLoS Pathog 7, 2011, el 002383.

Panni et al: "In vitro evolution of recognition specificity mediated by SH3 domains reveals target recognition rules." J Biol Chem 277, 2002, pp. 21666-21674.

Pietrek et al: "Role of the Kaposi's sarcoma-associated herpesvirus K15 SH3 binding site in inflammatory signaling and B-cell activation." J Virol 84, 2010, pp. 8231-8240.

Saksela et al: "SH3 domain ligand binding: What's the consensus and where's the specificity" FEBS Lett 586, 2012, pp. 2609-2614.

Schlatter et al "Generation, characterization and structural data of chymase binding proteins based on the human Fyn kinase SH3 domain." mAbs 4, 2012, pp. 497-508.

Schmaier et al: "Molecular primino of Lyn by GPVI enables an immune receptor to adopt a hemostatic role." Proc Nati Acad Sci USA 106, 2009, pp. 21167-21172.

Sicheri et al: "Structures of Src-family tyrosine kinases." Current opinion in structural biology 7, 1997, pp. 777-785.

Thompson et al: "Dystroglycan, TksS and Src mediated assembly of podosomes in myoblasts" PLoS One 3, 2008, e3638.

Thompson et al: "Modulation of cell spreading and cell-substrate adhesion dynamics by dystroglycan." J Cell Sci 123, 2010, pp. 118-127.

Tonikian et al: "Identifying specificity profiles for peptide recognition modules from phage-displayed peptide libraries." Nature Protocols 2, 2007, pp. 1368-1386.

Weidle et al: "The emerging role of new protein scaffold-based agents for treatment of cancer." Cancer genomics & proteomics 10, 2013, pp. 155-166.

Vingadassalom et al: "Insulin receptor tyrosine kinase substrate links the *E. coli* 0157:H7 actin assembly effectors Tir and EspF(U) during pedestal formation." Proc Nati Acad Sci USA 106: 2009, pp. 6754-6759.

Voss et al: "Identification of SH3 domain interaction partners of human FasL (CD178) by phage display screening." BMC immunology 10, 2009, pp. 53.

* cited by examiner

SEQUENCE LISTING

```
<160> NUMBER OF SEQ ID NOS: 21

<210> SEQ ID NO 1
<211> LENGTH: 57
<212> TYPE: PRT
<213> ORGANISM: Homo sapiens
<220> FEATURE:
<223> OTHER INFORMATION: NPHP1-SH3

<400> SEQUENCE: 1

Glu Glu Tyr Ile Ala Val Gly Asp Phe Thr Ala Gln Gln Val Gly Asp
1               5                   10                  15

Leu Thr Phe Lys Lys Gly Glu Ile Leu Leu Val Ile Glu Lys Lys Pro
            20                  25                  30

Asp Gly Trp Trp Ile Ala Lys Asp Ala Lys Gly Asn Glu Gly Leu Val
        35                  40                  45

Pro Arg Thr Tyr Leu Glu Pro Tyr Ser
    50                  55

<210> SEQ ID NO 2
<211> LENGTH: 57
<212> TYPE: PRT
<213> ORGANISM: Homo sapiens
<220> FEATURE:
<223> OTHER INFORMATION: Tec-SH3

<400> SEQUENCE: 2

Glu Ile Val Val Ala Met Tyr Asp Phe Gln Ala Ala Glu Gly His Asp
1               5                   10                  15

Leu Arg Leu Glu Arg Gly Gln Glu Tyr Leu Ile Leu Glu Lys Asn Asp
            20                  25                  30

Val His Trp Trp Arg Ala Arg Asp Lys Tyr Gly Asn Glu Gly Tyr Ile
        35                  40                  45

Pro Ser Asn Tyr Val Thr Gly Lys Lys
    50                  55

<210> SEQ ID NO 3
<211> LENGTH: 58
<212> TYPE: PRT
<213> ORGANISM: Homo sapiens
<220> FEATURE:
<223> OTHER INFORMATION: Fyn-SH3

<400> SEQUENCE: 3

Thr Leu Phe Val Ala Leu Tyr Asp Tyr Glu Ala Arg Thr Glu Asp Asp
1               5                   10                  15
```

```
Leu Ser Phe His Lys Gly Glu Lys Phe Gln Ile Leu Asn Ser Ser Glu
                20                  25                  30

Gly Asp Trp Trp Glu Ala Arg Ser Leu Thr Thr Gly Thr Gly Tyr
                35                  40                  45

Ile Pro Ser Asn Tyr Val Ala Pro Val Asp
            50                  55

<210> SEQ ID NO 4
<211> LENGTH: 57
<212> TYPE: PRT
<213> ORGANISM: Homo sapiens
<220> FEATURE:
<223> OTHER INFORMATION: Hck-SH3

<400> SEQUENCE: 4

Ile Ile Val Val Ala Leu Tyr Asp Tyr Glu Ala Ile His His Glu Asp
1               5                   10                  15

Leu Ser Phe Gln Lys Gly Asp Gln Met Val Val Leu Glu Glu Ser Gly
                20                  25                  30

Glu Trp Trp Lys Ala Arg Ser Leu Ala Thr Arg Lys Glu Gly Tyr Ile
                35                  40                  45

Pro Ser Asn Tyr Val Ala Arg Val Asp
            50                  55

<210> SEQ ID NO 5
<211> LENGTH: 71
<212> TYPE: PRT
<213> ORGANISM: Homo sapiens
<220> FEATURE:
<223> OTHER INFORMATION: Amph-SH3

<400> SEQUENCE: 5

Tyr Lys Val Glu Thr Leu His Asp Phe Glu Ala Ala Asn Ser Asp Glu
1               5                   10                  15

Leu Thr Leu Gln Arg Gly Asp Val Val Leu Val Val Pro Ser Asp Ser
                20                  25                  30

Glu Ala Asp Gln Asp Ala Gly Trp Leu Val Gly Val Lys Glu Ser Asp
                35                  40                  45

Trp Leu Gln Tyr Arg Asp Leu Ala Thr Tyr Lys Gly Leu Phe Pro Glu
            50                  55                  60

Asn Phe Thr Arg Arg Leu Asp
65                  70

<210> SEQ ID NO 6
<211> LENGTH: 64
<212> TYPE: PRT
<213> ORGANISM: Homo sapiens
<220> FEATURE:
<223> OTHER INFORMATION: RIMBP3-SH3

<400> SEQUENCE: 6

Lys Ile Met Ile Ala Ala Leu Asp Tyr Asp Pro Gly Asp Gly Gln Met
1               5                   10                  15

Gly Gly Gln Gly Lys Gly Arg Leu Ala Leu Arg Ala Gly Asp Val Val
                20                  25                  30

Met Val Tyr Gly Pro Met Asp Asp Gln Gly Phe Tyr Tyr Gly Glu Leu
                35                  40                  45

Gly Gly His Arg Gly Leu Val Pro Ala His Leu Leu Asp His Met Ser
            50                  55                  60
```

<210> SEQ ID NO 7
<211> LENGTH: 60
<212> TYPE: PRT
<213> ORGANISM: Homo sapiens
<220> FEATURE:
<223> OTHER INFORMATION: IRTKS-SH3

<400> SEQUENCE: 7

Gln Lys Val Lys Thr Ile Phe Pro His Thr Ala Gly Ser Asn Lys Thr
1               5                   10                  15

Leu Leu Ser Phe Ala Gln Gly Asp Val Ile Thr Leu Leu Ile Pro Glu
            20                  25                  30

Glu Lys Asp Gly Trp Leu Tyr Gly Glu His Asp Val Ser Lys Ala Arg
        35                  40                  45

Gly Trp Phe Pro Ser Ser Tyr Thr Lys Leu Leu Glu
    50                  55                  60

<210> SEQ ID NO 8
<211> LENGTH: 58
<212> TYPE: PRT
<213> ORGANISM: Homo sapiens
<220> FEATURE:
<223> OTHER INFORMATION: SNX30-SH3

<400> SEQUENCE: 8

Leu Lys Gly Arg Ala Leu Tyr Asp Phe His Ser Glu Asn Lys Glu Glu
1               5                   10                  15

Ile Ser Ile Gln Gln Asp Glu Asp Leu Val Ile Phe Ser Glu Thr Ser
            20                  25                  30

Leu Asp Gly Trp Leu Gln Gly Gln Asn Ser Arg Gly Glu Thr Gly Leu
        35                  40                  45

Phe Pro Ala Ser Tyr Val Glu Ile Val Arg
    50                  55

<210> SEQ ID NO 9
<211> LENGTH: 56
<212> TYPE: PRT
<213> ORGANISM: Homo sapiens
<220> FEATURE:
<223> OTHER INFORMATION: Eps8L1-SH3

<400> SEQUENCE: 9

Lys Trp Val Leu Cys Asn Tyr Asp Phe Gln Ala Arg Asn Ser Ser Glu
1               5                   10                  15

Leu Ser Val Lys Gln Arg Asp Val Leu Glu Val Leu Asp Asp Ser Arg
            20                  25                  30

Lys Trp Trp Lys Val Arg Asp Pro Ala Gly Gln Glu Gly Tyr Val Pro
        35                  40                  45

Tyr Asn Ile Leu Thr Pro Tyr Pro
    50                  55

<210> SEQ ID NO 10
<211> LENGTH: 59
<212> TYPE: PRT
<213> ORGANISM: Homo sapiens
<220> FEATURE:
<223> OTHER INFORMATION: FISH#5-SH3

<400> SEQUENCE: 10

Asp Val Tyr Val Ser Ile Ala Asp Tyr Glu Gly Asp Glu Glu Thr Ala
1               5                   10                  15

Gly Phe Gln Glu Gly Val Ser Met Glu Val Leu Glu Arg Asn Pro Asn 20                  25                  30

Gly Trp Trp Tyr Cys Gln Ile Leu Asp Gly Val Lys Pro Phe Lys Gly
            35                  40                  45

Trp Val Pro Ser Asn Tyr Leu Glu Lys Lys Asn
        50                  55

<210> SEQ ID NO 11
<211> LENGTH: 57
<212> TYPE: PRT
<213> ORGANISM: Homo sapiens
<220> FEATURE:
<223> OTHER INFORMATION: CMS#1-SH3

<400> SEQUENCE: 11

Val Asp Tyr Ile Val Glu Tyr Asp Tyr Asp Ala Val His Asp Asp Glu
1               5                   10                  15

Leu Thr Ile Arg Val Gly Glu Ile Ile Arg Asn Val Lys Lys Leu Gln
            20                  25                  30

Glu Glu Gly Trp Leu Glu Gly Glu Leu Asn Gly Arg Arg Gly Met Phe
        35                  40                  45

Pro Asp Asn Phe Val Lys Glu Ile Lys
    50                  55

<210> SEQ ID NO 12
<211> LENGTH: 56
<212> TYPE: PRT
<213> ORGANISM: Homo sapiens
<220> FEATURE:
<223> OTHER INFORMATION: OSTF1-SH3

<400> SEQUENCE: 12

Lys Val Phe Arg Ala Leu Tyr Thr Phe Glu Pro Arg Thr Pro Asp Glu
1               5                   10                  15

Leu Tyr Phe Glu Glu Gly Asp Ile Ile Tyr Ile Thr Asp Met Ser Asp
            20                  25                  30

Thr Asn Trp Trp Lys Gly Thr Ser Lys Gly Arg Thr Gly Leu Ile Pro
        35                  40                  45

Ser Asn Tyr Val Ala Glu Gln Ala
    50                  55

<210> SEQ ID NO 13
<211> LENGTH: 6
<212> TYPE: PRT
<213> ORGANISM: Homo sapiens
<220> FEATURE:
<223> OTHER INFORMATION: RT-loop sequence of NPHP1-SH3

<400> SEQUENCE: 13

Thr Ala Gln Gln Val Gly
1               5

<210> SEQ ID NO 14
<211> LENGTH: 54
<212> TYPE: DNA
<213> ORGANISM: Artificial Sequence
<220> FEATURE:
<223> OTHER INFORMATION: An oligonucleotide used for the generation of
      drHck-SH3 library
<220> FEATURE:
<221> NAME/KEY: variation
<222> LOCATION: 20,21,23,24,26,27,29,30,32,33,35,36
<223> OTHER INFORMATION: /replace="a"
      /replace="g"
      /replace="c"

```
        /replace="t"

<400> SEQUENCE: 14
agaacgtgct tccaccagng ngnngnngnn gnngnnagat tcttccagaa cgac          54

<210> SEQ ID NO 15
<211> LENGTH: 58
<212> TYPE: DNA
<213> ORGANISM: Artificial Sequence
<220> FEATURE:
<223> OTHER INFORMATION: An oligonucleotides used for the generation of
      drHck-SH3 library
<220> FEATURE:
<221> NAME/KEY: variation
<222> LOCATION: 21,22,24,25,27,28,30,31,33,34,36,37
<223> OTHER INFORMATION: /replace="a"
        /replace="g"
        /replace="c"
        /replace="t"

<400> SEQUENCE: 15
gtgctttcca ccattcaccg nngnngnngn ngnngnncag aacgaccatc tgatcacc       58

<210> SEQ ID NO 16
<211> LENGTH: 60
<212> TYPE: PRT
<213> ORGANISM: Artificial Sequence
<220> FEATURE:
<223> OTHER INFORMATION: NPHP1-drSH3 sequence with randomized loop
      residues

<400> SEQUENCE: 16

Glu Glu Tyr Ile Ala Val Gly Asp Phe Cys Thr Tyr Thr Gly Pro Asp
1               5                   10                  15

Leu Thr Phe Lys Lys Gly Glu Ile Leu Leu Val Ile Glu Arg Pro Phe
            20                  25                  30

Ala His Thr Asp Gly Trp Trp Ile Ala Lys Asp Ala Lys Gly Asn Glu
        35                  40                  45

Gly Leu Val Pro Arg Thr Tyr Leu Glu Pro Tyr Ser
    50                  55                  60

<210> SEQ ID NO 17
<211> LENGTH: 60
<212> TYPE: PRT
<213> ORGANISM: Artificial Sequence
<220> FEATURE:
<223> OTHER INFORMATION: NPHP1-drSH3 sequence with randomized loop
      residues

<400> SEQUENCE: 17

Glu Glu Tyr Ile Ala Val Gly Asp Phe Gln Pro Ser Met Pro Cys Asp
1               5                   10                  15

Leu Thr Phe Lys Lys Gly Glu Ile Leu Leu Val Ile Glu Gln Leu Gln
            20                  25                  30

Met Cys Leu Asp Gly Trp Trp Ile Ala Lys Asp Ala Lys Gly Asn Glu
        35                  40                  45

Gly Leu Val Pro Arg Thr Tyr Leu Glu Pro Tyr Ser
    50                  55                  60

<210> SEQ ID NO 18
<211> LENGTH: 60
<212> TYPE: PRT
<213> ORGANISM: Artificial Sequence
<220> FEATURE:
<223> OTHER INFORMATION: TEC-drSH3 sequence with randomized loop
``` residues

<400> SEQUENCE: 18

Glu Ile Val Val Ala Met Tyr Asp Phe Met Ser Asn Ser Val His Asp
1               5                   10                  15

Leu Arg Leu Glu Arg Gly Gln Glu Tyr Leu Ile Leu Glu Lys Gln Asp
            20                  25                  30

Lys Arg Gly Val His Trp Trp Arg Ala Arg Asp Lys Tyr Gly Asn Glu
        35                  40                  45

Gly Tyr Ile Pro Ser Asn Tyr Val Thr Gly Lys Lys
    50                  55                  60

<210> SEQ ID NO 19
<211> LENGTH: 63
<212> TYPE: PRT
<213> ORGANISM: Artificial Sequence
<220> FEATURE:
<223> OTHER INFORMATION: NPHP1-drSH3 sequence selected from the library
      of randomized loop residues

<400> SEQUENCE: 19

Glu Glu Tyr Ile Ala Val Gly Asp Phe Tyr Gly Cys Asp Pro Val Asp
1               5                   10                  15

Leu Thr Phe Lys Lys Gly Glu Ile Leu Val Ile Glu Lys Lys Pro
            20                  25                  30

Ser Phe Val Trp Ile Pro Asp Gly Trp Trp Ile Ala Lys Asp Ala Lys
        35                  40                  45

Gly Asn Glu Gly Leu Val Pro Arg Thr Tyr Leu Glu Pro Tyr Ser
    50                  55                  60

<210> SEQ ID NO 20
<211> LENGTH: 63
<212> TYPE: PRT
<213> ORGANISM: Artificial Sequence
<220> FEATURE:
<223> OTHER INFORMATION: TEC-drSH3 sequence selected from the library of
      randomized loop residues

<400> SEQUENCE: 20

Glu Ile Val Val Ala Met Tyr Asp Phe Asn Thr Ser Ser Trp Trp Asp
1               5                   10                  15

Leu Arg Leu Glu Arg Gly Gln Glu Tyr Leu Ile Leu Glu Lys Asn Ser
            20                  25                  30

Ser Phe Lys Phe His Asp Val His Trp Trp Arg Ala Arg Asp Lys Tyr
        35                  40                  45

Gly Asn Glu Gly Tyr Ile Pro Ser Asn Tyr Val Thr Gly Lys Lys
    50                  55                  60

<210> SEQ ID NO 21
<211> LENGTH: 63
<212> TYPE: PRT
<213> ORGANISM: Artificial Sequence
<220> FEATURE:
<223> OTHER INFORMATION: Tec-drSH3 sequence selected from the library of
      randomized loop residues

<400> SEQUENCE: 21

Glu Ile Val Val Ala Met Tyr Asp Phe His Ser Thr Pro Trp Trp Asp
1               5                   10                  15

Leu Arg Leu Glu Arg Gly Gln Glu Tyr Leu Ile Leu Glu Lys Asn Ser
            20                  25                  30

```
Ser Phe Thr Leu Trp Asp Val His Trp Trp Arg Ala Arg Asp Lys Tyr
        35                  40                  45

Gly Asn Glu Gly Tyr Ile Pro Ser Asn Tyr Val Thr Gly Lys Lys
    50                  55                  60
```

SH3 DOMAIN DERIVATIVES

FIELD OF THE INVENTION

The present invention is directed to the field of engineered binding proteins. Particularly, the present invention is directed to SH3 domain derivatives having a specific binding affinity to a target molecule. In this respect, the invention provides SH3 domain derivatives of the ciliary adaptor protein nephrocystin (NPHP1) and the Tec kinase. The invention also provides a method for the production of a library comprising recombinant derivatives of NPHP1 or Tec SH3 domains, and a method for selecting from such libraries one or more derivatives of the SH3 domain of NPHP1 or Tec having a specific binding affinity to a target molecule.

BACKGROUND OF THE INVENTION

Antibodies are the most widely exploited class of binding proteins with desired specificities used in research, biotechnology, and medical applications, such as diagnostic tests and biopharmaceutical therapeutics. However, during recent years there has been increasing interest in replacing antibodies in these applications with non-immunoglobulin-derived engineered ligand binding proteins, often collectively referred to as scaffold proteins (reviewed in Weidle et al, 2013; Gebauer & Skerra, 2009; Binz & Pluckthun, 2005; Hey et al, 2005).

As discussed in these reviews, by combining modern synthetic biochemistry and affinity selection methods of large molecular libraries (such as phage display libraries) many different proteins backbones can be used as scaffolds to develop artificial binding proteins that can be targeted to virtually any ligand of interest with high affinity and specificity. Scaffold proteins can be smaller than the simplest antibody fragments used for biomedical targeting, and they can have several other advantages compared to antibodies related to their biophysical properties (such as stability and manufacturability). Ligand-targeted scaffold proteins can also be fused with antibodies or antibody fragments to create bi- or multispecific binding proteins (e.g. Järviluoma et al, 2012). In such applications the favorable biophysical properties of scaffold proteins can be especially beneficial, since constructing multispecific proteins via antibody fragment fusions may lead to challenging expression and solubility profiles.

A promising scaffold protein approach is based on a ubiquitous protein interaction module known as the Src homology-3 (SH3) domain. The SH3 domain is a small (typically ≈60 aa) protein interaction module composed of a β-sandwich consisting of five strands connected by three loops and a short $3_{10}$ helix. The human genome encodes approximately 300 different SH3 domains that share this structure, and serve to guide interactions of their host proteins with their targets to regulate various cellular processes (Li, 2005; Macias et al, 2002; Mayer, 2001; Mayer & Saksela, 2005).

Two loop regions in the SH3 fold (RT-loop and n-src-loop) contribute to binding specificity in these natural protein interactions (Saksela & Permi, 2012). As described in patent U.S. Pat. No. 6,794,144 (and in Hiipakka & Saksela, 2007) the natural binding specificity of the SH3 domain of the human tyrosine kinase Hck can be altered via engineering of its RT-loop residues, and Hck-SH3 retargeted to bind to novel ligands. This engineering was achieved by creating a large phage-display library where six residues in the RT-loop of Hck-SH3 were replaced with random amino acids combinations followed by affinity selection of clones with the desired binding specificity out of this SH3 scaffold library.

As noted in U.S. Pat. No. 6,794,144 engineering of the RT-loop can be combined by similar manipulation of additional SH3 residues, such as the n-src-loop, to further enhance the re-targeting potential of the SH3 scaffold. Such a double-loop engineering approach was described in 2007 by Neri and colleagues for the SH3 domain of the human Fyn tyrosine kinase (Grabulovski et al, 2007), another member of the Src kinase family and a close relative of Hck (see Sicheri & Kuriyan, 1997). Grabulovski et al dubbed the novel binder molecules based on the Fyn-SH3 scaffold as Fynomers, which they have subsequently used successfully to target several proteins, such as chymase (Schlatter et al, 2015) and to create bispecific SH3-IgG fusion proteins called FynomAbs (Brack et al, 2014). One such FynomAb that targets TNF and IL-17A (COV322) is the lead product of the Swiss biotech company Covagen, and has reached to Phase 1b clinical trials (www.covagen.com/pipeline/cova322/).

Further, high affinity binding proteins comprising modified SH3 domains of Fyn kinase are disclosed in WO2008022759. The SH3 domains were modified so that at least one amino acid in the src loop and at least one amino acid in the RT loop were substituted, deleted or added. WO2013135588 and WO2014170063 disclose binding molecules with antitumoral activity binding to two different epitopes of an antigen, wherein the binding molecule comprises a Fyn SH3-derived polypeptide.

Despite the promise of engineered SH3 domains and other scaffold proteins introduced above, regular antibodies and their fusions are still overwhelmingly dominating the field of biopharmaceutical development. In order to change this situation and to fully unfold the potential of the scaffold technologies their robustness and general applicability should still be improved. The key parameters of robustness in this regard are the quality (binding affinity) of the primary binders selected from a library as well as the time and effort needed for such screens, which together translate into the ease and likelihood of finding potent lead molecules against diverse therapeutic targets.

So far only the two Src-family SH3 domains Hck and Fyn have been used as scaffolds for creating libraries for engineering of novel binding specificities (see references above). In addition, the SH3 domain of Abl, another tyrosine kinase, has been used in a smaller scale for a related purpose in a study aimed at elucidation of determinants of natural SH3 binding specificity (Panni et al, 2002). Based on the shared three-dimensional structure common to all SH3 domains, it could be expected that all 300 human SH3 domains would perform very similarly as backbones of SH3 scaffold libraries, but this assumption has not been experimentally confirmed or systematically tested.

However, a phage-display library consisting of an almost complete repertoire (n=296) of human SH3 domains in their native form has been generated, and successfully used for affinity selection of preferred SH3 domain partners for a large number of known or suspected natural SH3 ligand proteins (Amako et al, 2013; Antoku et al, 2008; Asbach et al, 2012; Ebsen et al, 2014; Heikkinen et al, 2008; Igloi et al, 2015; Kesti et al, 2007; Kleino et al, 2009, Kleino et al, 2015; Kärkkäinen et al, 2006; Neuvonen et al, 2011; Pietrek et al, 2010; Schmaier et al, 2009; Thompson et al, 2008; Thompson et al, 2009; Vingadassalon et al, 2009, Voss et al, 2009). These studies have shown that at least a large proportion of all human SH3 domains can be displayed on the surface of the M13 filamentous phage in a functional form, and thus validated many of them as potential backbones for construction of new loop-randomized SH3 scaffold phage-display libraries.

SUMMARY OF THE INVENTION

One of the objects of the present invention is to provide a recombinant binding protein having a specific Src homology 3 (SH3) domain based binding affinity to a target molecule, said binding protein comprising a nephrocystin (NPHP1) derived SH3 domain, wherein a) at least one amino acid is substituted in the RT-loop of said SH3 domain or added to the RT-loop, and/or b) at least one amino acid is substituted in the n-src-loop of said SH3 domain or added to the n-src-loop, and wherein said nephrocystin (NPHP1) derived SH3 domain has an amino acid sequence having at least 85% sequence identity to the amino acid sequence of SEQ ID NO:1 outside the RT-loop and n-src-loop.

Another object of the present invention is to provide a recombinant binding protein having a specific Src homology 3 (SH3) domain based binding affinity to a target molecule, said binding protein comprising the Tec kinase derived SH3 domain, wherein a) at least one amino acid is substituted in the RT-loop of said SH3 domain or added to the RT-loop, and/or b) at least one amino acid is substituted in the n-src-loop of said SH3 domain or added to the n-src-loop, and wherein said Tec kinase derived SH3 domain has an amino acid sequence having at least 85% sequence identity to the amino acid sequence of SEQ ID NO:2 outside the RT-loop and n-src-loop.

Another object of the present invention is to provide a method for the production of a library comprising recombinant derivatives of the SH3 domain of NPHP1 or the Tec kinase having the sequence of SEQ ID NO: 1 or 2, respectively, said method comprising the steps of (a) generating recombinant derivatives of the SH3 domain of SEQ ID NO: 1 or 2 by substituting or adding at least one amino acid in the RT loop of said SH3 domain, and/or substituting or adding at least one amino acid in the n-src-loop of said SH3 domain, and (b) building a library comprising the recombinant derivatives of the SH3 domain generated in step (a); wherein the recombinant derivatives of the SH3 domain of retain at least 85% identity to the amino acid of SEQ ID NO: 1 or 2 outside the RT and n-src loops; and wherein the RT loop is located at amino acid positions 8-17 of SEQ ID NO: 1 or 2, and the n-src loop is located at amino acid positions 28-34 of SEQ ID NO: 1 or 2.

The present invention also provides libraries of SH3 derivatives obtained by the above method, and methods for selecting from these libraries one or more derivatives of the SH3 domains having a specific binding affinity to a desired target molecule.

One of the further objects of the invention is to provide polynucleotides, vectors and host cells for the production of the binding proteins.

DETAILED DESCRIPTION OF THE PRESENT INVENTION

Figure 1:
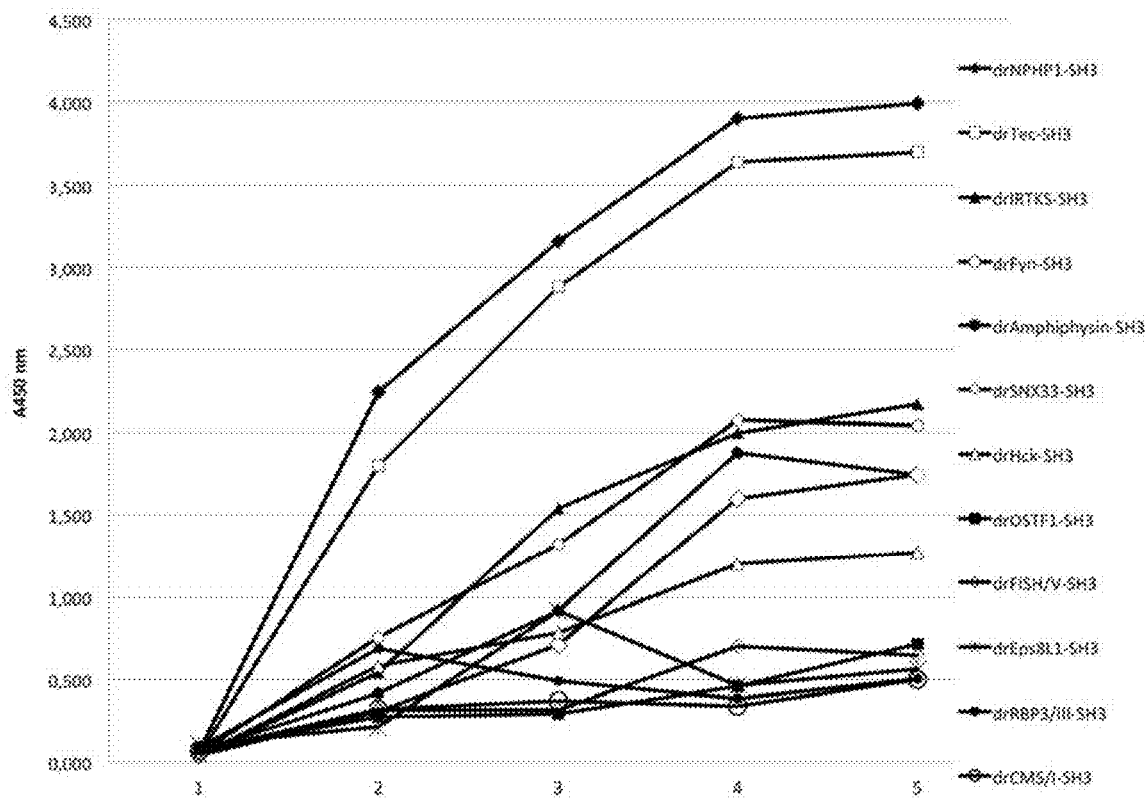
FIG. 1. Enrichment of phages showing reactivity against the NS1 antigen of Dengue-2 virus during panning rounds 1 to 5 of different drSH3 phage display libraries. The phage populations present in the affinity selection process during successive rounds of panning of the indicated drSH3 libraries were analyzed by phage-ELISA on immobilized NS1. An equal quantity of infectious phages from each panning round was allowed to bind to immobilized Dengue-2 virus NS1 antigen followed by detection using an anti-M13-HRP conjugate.

In this invention, the performance of drSH3 libraries constructed based on a representative panel of 12 different SH3 domains (see Table 1) selected from the complete human SH3 repertoire was compared by panning against different target molecules such as Dengue-2 virus NS1, Malaria HRP-II, CTLA-4 and Her2 proteins. Surprisingly, when libraries of similar size and complexity were constructed using a strategy for RT- and n-src-loop randomization analogous for all the different SH3 domain backbones, and an equal quantity of each infectious drSH3 library phage was used for affinity selection against the target proteins, libraries based on the SH3 domains of NPHP1 and the Tec kinase gave much more effectively rise to high affinity binders for the target molecules than any other drSH3 library tested in this invention. Of note, one of the 10 other human SH3 domain scaffolds tested was the Fyn SH3 domain, which was randomized in its RT- and n-src-loops using a strategy identical to that described in previous work on Fynomers discussed above representing the current state of the art in the area.

The superior targeting potential of the NPHP1- and Tec-based drSH3 libraries was clearly evident both when comparing the enrichment of reactivity against the target proteins in affinity-selected populations of phages from different rounds of panning of the individual drSH3 libraries, as well as when identifying the SH3 backbone of the selected clones when equal amounts of the different drSH3 libraries where mixed together and panned against the target proteins in a competitive fashion.

The excellent targeting capacity of the NPHP1 and Tec SH3 scaffolds was not limited to drSH3 libraries constructed based on the initially applied strategy for randomization of the RT- and n-src-loop regions presented in Table 1, as libraries with at least similar performance could be generated by other strategies, such as modifying the n-src loop region via insertion of a random peptide instead of a substitution, as shown in Table 2.

Therefore, the present invention is directed to a recombinant binding protein having a specific Src homology 3 (SH3) domain based binding affinity to a target molecule, said binding protein comprising a nephrocystin (NPHP1) derived SH3 domain, wherein a) at least one amino acid is substituted in the RT-loop of said SH3 domain or added to the RT-loop, and/or b) at least one amino acid is substituted in the n-src-loop of said SH3 domain or added to the n-src-loop, and wherein said nephrocystin (NPHP1) derived SH3 domain has an amino acid sequence having at least 85%, preferably 90% or 95% sequence identity to the amino acid sequence of SEQ ID NO:1 outside the RT-loop and n-src-loop, The present invention is also directed to a recombinant binding protein comprising the Tec kinase derived SH3 domain, wherein a) at least one amino acid is substituted in the RT-loop of said SH3 domain or added to the RT-loop, and/or b) at least one amino acid is substituted in the n-src-loop of said SH3 domain or added to the n-src-loop, and wherein said Tec kinase derived SH3 domain has an amino acid sequence having at least 85%, preferably 90% or 95% sequence identity to the amino acid sequence of SEQ ID NO:2 outside the RT-loop and n-src-loop.

The main strategy in the modification of the RT-loop and n-src-loop is to substitute or add amino acids in the loop. Preferably, at least two, three, four, five or six amino acids are substituted in the RT-loop of said SH3 domains or added to the RT-loop. Preferably, at least two, three, four, five or six amino acids are substituted in the n-src-loop of said SH3 domains or added to the n-src-loop. However, the original length or composition of the loop does not need to be maintained, and residues in some positions of the loops may also be completely deleted, i.e. the deleted amino acid residue(s) is/are substituted by next adjacent remaining amino acid residue in the loop.

In this invention, the location of the RT loop in the NPHP1 SH3 domain corresponds to amino acid positions 8-17 of SEQ ID NO:1, preferably 10-15 of SEQ ID NO:1. The n-src-loop in the NPHP1 SH3 domain is defined to locate between the amino acid positions 28-34 of SEQ ID NO:1, preferably 30-32 of SEQ ID NO:1.

The location of the RT loop in the Tec kinase SH3 domain corresponds to amino acid positions 8-17 of SEQ ID NO:2, preferably 10-15 of SEQ ID NO:2. The n-src-loop in the Tec kinase SH3 domain is defined to locate between the amino acid positions 28-34 of SEQ ID NO:2, preferably 30-32 of SEQ ID NO:1.

It is also noted that the amino acid sequence outside the RT-loop and n-src-loop in both NPHP1 SH3 domain and the Tec kinase SH3 domain is rather unique compared to other known SH3 domains. Therefore, the group of SH3 domains with an amino acid sequence having at least 85%, preferably 90% or 95% sequence identity to the amino acid sequence of SEQ ID NO:1 or 2 outside the RT-loop and n-src-loop does not comprise other known SH3 domains having their natural amino acid sequences.

In principle, high affinity binders for various types of target molecules can be selected from the SH3-based libraries of the invention. Preferably, the selected high affinity binder protein, said recombinant binding protein or the fusion protein defined below, has a specific binding affinity to a target molecule of $10^{-5}$ to $10^{-12}$ M, more preferably $10^{-6}$ to $10^{-12}$ M, $10^{-7}$ to $10^{-12}$ M or $10^{-8}$ to $10^{-12}$ M. The target molecule is preferably a protein or a peptide. Particular examples of the target proteins are human serum albumin (HSA), Her2, Her3, CTLA-4, PD-1, PD-L1, PD-L2, LAG3, TIM-3, VISTA, CD73, CD39, CD3, CD8 and CD16A. Human serum albumin (HSA) is one of the more preferred targets in the present invention. The target molecule is preferably not a natural NPHP1 or the Tec kinase SH3 domain binding ligand. Examples of other target molecules than proteins or peptides are small organic or non-amino-acid based compounds such as monosaccharides, oligo- or polysaccharides, and fatty acids, etc.

The present invention also provides a fusion protein comprising a binding protein as defined above. Preferably, the binding protein is fused with another protein such as an antibody or a fragment thereof. However, the specific targeting properties of the binding proteins of the present invention also allow for substituting antibodies in the known fusion proteins comprising an antibody or a fragment thereof. The binding protein may also be fused to any pharmaceutically and/or diagnostically active component, which may be a non-polypeptide component such as a label.

The present invention also provides a polynucleotide coding for the recombinant binding proteins described as well as vectors comprising said polynucleotide. For the production of binding proteins selected from the SH3-based libraries of the invention, one can use a host cell comprising said polynucleotide and/or a vector comprising said polynucleotide.

The present invention is further directed to a method for the production of a library comprising recombinant derivatives of the SH3 domain of NPHP1 or the Tec kinase having the sequence of SEQ ID NO: 1 or 2, respectively, said method comprising the steps of (a) generating recombinant derivatives of the SH3 domain of SEQ ID NO: 1 or 2 by substituting or adding at least one amino acid in the RT loop of said SH3 domain, and/or substituting or adding at least one amino acid in the n-src-loop of said SH3 domain, and (b) building a library comprising the recombinant derivatives of the SH3 domain generated in step (a); wherein the recombinant derivatives of the SH3 domain of retain at least 85% identity to the amino acid of SEQ ID NO: 1 or 2 outside the RT and n-src loops; and wherein the RT loop is located at amino acid positions 8-17 of SEQ ID NO: 1 or 2, and the n-src loop is located at amino acid positions 28-34 of SEQ ID NO: 1 or 2.

As shown in the Experimental Section, one of the preferred modification strategies for the present method is the following: in step (a) six amino acids in the RT loop are randomly substituted, and up to four amino acids in the n-src loop are substituted with six random residues. In Table 2, other examples of randomization strategies for NPHP1-SH3 and Tec-SH3 libraries are shown. For instance, the RT loop sequence TAQQVG (SEQ ID NO: 13) in NPHP1-SH3 is preferably substituted with six or eight randomized amino acids. The n-src-loop sequence KKP of NRHP1-SH3 is preferably modified so that six or eight randomized amino acids are added to the loop while one or more of the amino acids in the KKP sequence remain(s) in the loop.

It is clear that a person skilled in the art can easily use different modification strategies in order to achieve the effect of the invention. To facilitate the construction process, one may also design SH3 libraries wherein only RT loop or n-src-loop is modified, as in our experience specific target binding with sufficient affinity for many applications can be achieved using such a simplified SH3 engineering scheme.

The present invention also provides libraries of SH3 derivatives obtained by the above method. Preferably, the libraries comprise dubbed drSH3 domains, i.e. they are preferably double-randomized in the RT-loop as well as n-src-loop regions.

The library produced by the above method is preferably a phage display library. A "phage display library" is a collection of phages that have been genetically engineered to express a set of potential targeting peptides, such as SH3 domain derivatives, on their outer surface. In order to build a phage display library expressing SH3 domain derivatives, partly randomized set of DNA sequences encoding the SH3 domains are inserted in frame into a gene encoding a phage capsule protein. In the case of M13 filamentous phage display, the DNA encoding the binding protein or peptide of interest is ligated into the pIII or pVIII gene, encoding either the minor or major coat protein, respectively. Various methods of phage display and methods for producing diverse populations of peptides are well known in the art. However, many alternative systems for displaying binding proteins/peptides for affinity selection are also well-known in the art, and could be used for construction of NPHP1- or Tec-based drSH3 libraries The present invention is also directed a method for selecting from a library comprising recombinant derivatives of the SH3 domain of NPHP1 or the Tec kinase, said method comprising the steps of (a) contacting the library comprising derivatives of the SH3 domain of NPHP1 or the Tec kinase with a target molecule under conditions and for a time sufficient to permit the derivatives and the target molecule to interact, wherein the target molecule is not a natural NPHP1 or the Tec kinase SH3 binding ligand, respectively; and (b) selecting from the library one or more derivatives of the SH3 domain of NPHP1 or the Tec kinase having a specific binding affinity to the target molecule, wherein the selected derivatives of the SH3 domain of NPHP1 or the Tec kinase retain at least 85% identity to the amino acid of SEQ ID NO: 1 or 2, respectively, outside the RT and n-src loops; and wherein the RT loop is located at amino acid positions 8-17 of SEQ ID NO: 1 or 2, respectively, and the n-src loop is located at amino acid positions 28-34 of SEQ ID NO: 1 or 2, respectively.

Preferably, the above method of selecting is performed by immobilizing a relevant target molecule to a solid surface, such as a microtiter well, so that when said solid surface is contacted with a phage that displays a SH3 domain derivative that binds to the target molecule the phage will remain while other phage are removed by washing. In the next step, those phages that remained are used to produce more phage by bacterial infection with a helper phage in order to produce an enriched phage mixture of relevant binding phage. The repeated cycling of these steps is referred to as 'panning'.

Although particular embodiments have been disclosed herein in detail, this has been done by way of example for purposes of illustration only, and is not intended to be limiting with respect to the scope of the appended claims that follow. In particular, it is contemplated by the inventor that various substitutions, alterations, and modifications may be made to the invention without departing from the scope of the invention as defined by the claims. For instance, the choice of protocols and buffers are believed to be a matter of routine for a person of ordinary skill in the art with knowledge of the embodiments described herein.

Having generally described the invention above, the same will be more readily understood by reference to the following Experimental Section, which is provided by way of illustration and is not intended as limiting.

Although methods and materials similar or equivalent to those described herein can be used in the practice or testing of the present invention, suitable methods and materials are described below. The materials, methods, and examples are illustrative only and not intended to be limiting.

Experimental Section

Materials and Methods

The following sections detail the techniques and reagents used for the generation of highly diverse phage-displayed drSH3 libraries using 12 different human SH3 domains (Hck-SH3 [Gene ID: 3055], Amphiphysin-SH3 [Gene ID: 273], RBP3/III-SH3 [Gene ID: 85376], IRTKS-SH3 [Gene ID: 55971], SNX33-SH3 [Gene ID: 257364], Eps8L1-SH3 [Gene ID: 54869], FISH/V-SH3 [Gene ID: 9644], CMS/I-SH3 [Gene ID: 23607], OSTF1-SH3 [Gene ID: 26578], Fyn-SH3 [Gene ID: 2534], NPHP1-SH3 [Gene ID: 4867], Tec-SH3 [Gene ID: 7006]) as display scaffolds. The relative performance of these drSH3 scaffold libraries was subsequently compared in an affinity selection process by monitoring the enrichment of specific drSH3 displaying phage clones against multiple target proteins of interest.

Construction of Double-Randomized drSH3 Phage Display Libraries

Critical component in the construction of a phage-displayed drSH3 library is a suitable vector system designed to display drSH3 domains as fusion proteins on the surface of M13 bacteriophage. Multiple vectors and formats are available for the construction of phage-displayed polypeptide libraries (Petrenko & Smith, 2005). For display of drSH3 libraries we have generated an optimized pUC119-based M13-phagemid vector pCA11N that allows selection both with ampicillin/carbenicillin as well as with chloramphenicol. Otherwise it contains the generic features of commonly used pIII-fusion display vectors, including a PelB signal sequence, and unique SfiI and NotI restriction enzyme sites for cloning of the codon-optimized drSH3 genes fused to the full-length pIII gene by the E-tag peptide sequence. The pCA11N phagemid contains a double-stranded DNA (dsDNA) origin of replication (dsDNA ori) and replicates as a double-stranded plasmid when inserted into an *E. coli* host. A single-stranded DNA (ssDNA) filamentous phage origin of replication (f1 ori) contains all of the DNA sequences necessary for packaging of the viral DNA into phage particles upon superinfection with a helper phage. While wild-type P3 is present at five copies per phage particle in total, the P3 fused drSH3 is expected to be displayed in a monovalent format. The phage-displayed drSH3 libraries were created by inserting a mutagenic oligonucleotides in-frame with the gene encoding the SH3 domain (see below). In addition to flanking sequences that are complementary to the SH3 domain, the mutagenic oligonucleotide contains a stretch of degenerate codons that encode the randomized peptides at RT and n-src loops.

drSH3 Library Design

The mutagenesis process applied for the generation of randomized library is the most critical step in phage display methodology. For library construction, a number of different mutagenesis methods have been developed, and reviewed in detail elsewhere (Fellouse & Pal, 2005). We prefer using oligonucleotide-directed mutagenesis and high-efficiency bacterial transformation to generate highly diverse libraries (Kunkel et al, 1987; Tonikian et al, 2007). For generation of completely random libraries, unique codons in the template DNA were replaced by NNK degenerate codons (where N=A/G/C/T and K=T/G), which encode all 20 natural amino acids. The TAG amber codon is suppressed by insertion of glutamine in a suppressor *E. coli* strain such as TG1 and XL-1 blue suitable for phage propagation. This is the simplest and most complete method for introducing diversity in a phage-derived library. Alternatively, incorporating degenerate codons encoding for only a subset of the natural amino acids can generate more restricted libraries. The randomization strategies used to generate drSH3 libraries with analogous RT- and n-src-loop modifications introduced into each SH3 framework are presented in Table 1. This randomization design corresponds to the strategy used in Grabulovski et al (2007), and the drFyn-SH3 library thus exactly matches with their Fyn-SH3 based library and the Fynomer-technology subsequently based on that study.

Mutagenesis for drSH3 Library Construction

The drSH3 phage display libraries were constructed by using the oligonucleotide-directed mutagenesis technique first described by Kunkel and colleagues (Kunkel et al, 1987), and later improved by Tonikian et al. (2007). In the first step, random mutations were introduced into an ssDNA template. The single-stranded phagemid DNA was purified from CJ236 dut⁻/ung⁻ E. coli strain, which specifically incorporates uracil instead of thymine in DNA. The uracil-containing ssDNA was used as a template onto which mutagenic oligonucleotides were annealed. The mutagenic oligonucleotides were designed such that they share a minimum of 15 nucleotide complementarity with the template both up- and downstream of the region targeted for mutagenesis to ensure efficient annealing. Examples of oligonucleotides used for the generation of drHck-SH3 library are shown below:

```
RT-loop:
                                        (SEQ ID NO: 14)
5'-AGAACGTGCTTTCCACCAGNNGNNGNNGNNGNNGNNAGATTCTTCCA
GAACGAC-3' n-Src-loop:
                                        (SEQ ID NO: 15)
5'-GTGCTTTCCACCATTCACCGNNGNNGNNGNNGNNGNNCAGAACGACC
ATCTGATCACC-3'
```

These oligonucleotides were designed to simultaneously introduce six random amino acids into both RT and n-Src loops of Hck SH3 domain. The oligonucleotides were annealed to the uracil-containing ssDNA template to prime the synthesis of a complementary DNA strand by T7 DNA polymerase. Subsequently, T4 ligase was used to form covalently linked circular dsDNA, containing mismatches in the region targeted for mutagenesis.

E. coli Electroporation and Production of drSH3 Library Phage

Covalently linked circular dsDNA was affinity-purified and transformed by high-efficiency electroporation into a dut⁺/ung⁺ SS320 E. coli host, which preferentially replicates the nascent DNA containing the mutagenic oligonucleotide instead of the uracil-containing parental strain. The E. coli SS320 strain has been designed for high-efficiency DNA transformation by mating MC1061 and XL1-blue and selecting on tetracycline and streptomycin medium (Sidhu et al, 2000). The strain thus encompasses the high-efficiency transformation qualities of MC1061, and contains the F' episome from XL1-blue, critical for bacteriophage infection and propagation. Once transformed into the SS320 host, the DNA is resolved through DNA repair and replication, and the resulting library is packaged into phage particles.

Affinity Panning of the drSH3 Libraries

The affinity selection process was conducted using standard solid phase sorting strategy (Sidhu et al, 2000; Viti et al, 2000). Specific phage-displayed drSH3-domains were selected for by panning against multiple diagnostically and therapeutically relevant target proteins including Dengue-2 virus non-structural protein-1 (NS1), Malaria histidine-rich protein II (HRP-II), cytotoxic T-lymphocyte-associated protein 4 (CTLA-4), human epidermal growth factor receptor 2 (Her2), and human serum albumin (HSA), which were produced in-house or obtained commercially.

The immobilized target proteins (20 µg/ml in PBS; Maxisorp Immunotubes, Nunc) were incubated in the presence of an equal quantity of infectious naïve drSH3 phage libraries (in 2.5% milk in PBS with 0.1% of Tween20 [PBS-MT]). Non-specific phages were removed by extensive washing with PBS-MT, and the remaining pool of phage were eluted and amplified in E. coli XL1-Blue host according to standard protocols (Tonikian et al, 2007; Viti et al, 2000). The amplified pool of phages was collected, and the process was reiterated up to five rounds to enrich for a pool of phage-displayed drSH3-domains specific to the target protein.

Individual phagemid clones were randomly picked from different rounds of affinity selection as needed in order to characterize their drSH3 inserts by DNA sequencing, and to generate homogenous phage preparations for binding studies (see below).

Binding Assay Based on Phage-ELISA

Complete populations of amplified phages obtained after 1-5 rounds of affinity panning or clonal phage supernatants produced by individual phagemid-carrying bacterial colonies from the fourth round of panning were tested for specific binding to their target proteins using a modification of the enzyme-linked immunosorbent assay (ELISA). In phage-ELISA the target protein and negative control protein (GST) were immobilized on an immunoplate. Affinity-selected phage populations or infectious progeny of individual phage clones were then incubated with the target protein- or GST-coated wells, non-bound phages were removed by washing, and a horse radish peroxidase (HRP) conjugated monoclonal antibody raised against the M13 phage particle was used to detect the specific phage binding to the target proteins. In addition to proteins of interest, the phages were allowed to bind to plates coated with polyclonal anti-E-tag antibody (LifeSpan BioSciences) to normalize the quantity of phage displaying drSH3-E-tag-P3 fusion protein on their surface instead of total phage. Testing of phage binding to GST again served as a negative control. Upon addition of the HRP substrate, binding of the clones was detected by a spectrophotometric readout.

Specifically, phage-ELISA was performed in 96-well Maxisorp microtiter plates (Nunc) coated over night at 4° C. with 100 µl of target and control proteins (5 µg/ml in PBS). The wells were washed 3× with PBS-0.05% Tween20 and blocked with 5% skimmed milk powder in PBS (milk-PBS) for 2 h at RT. Appropriate dilutions of drSH3-displaying phage pools or single phage clones were prepared in milk-PBS and incubated with the coated target protein for 1 h at RT followed by washes 5× with PBS-0.05% Tween20 to remove unbound phage. The detection was performed with HRP-conjugated mouse monoclonal anti-M13 antibody (GE Healthcare), and TMB (3,3' 5,5'-tetramethylbenzidine) substrate. The staining reaction was stopped with 1 M sulfuric acid and absorbance measured at 450 nm using Multiskan Ascent ELISA-reader (Thermo Fisher Scientific).

Results and Conclusions

Design and Construction of drSH3 Phage Library

To create large and highly diverse phage display libraries of drSH3 mutants, the RT and n-Src loops were combinatorially mutated in a group of 12 SH3 domains from 12 different human proteins, and compared as scaffolds for generating novel binding proteins. These 12 SH3 domains were selected among the complete human SH3 domain repertoire mainly based on two criteria. First, we made use of the extensive published and unpublished data that has accumulated over the years on the use of an SH3 domain phage display library created by Kärkkäinen et al (2006) containing a near complete collection (n=296) of unmodified native human SH3 domains, which has been extensively used to characterize natural SH3 interactions. Based on collective information from these studies we focused on SH3 domains that in their natural form have proven to be highly functional when displayed on the surface of M13 phages. Second, we considered the sequence homology relationships among the human SH3 domains, and chose 10 SH3 domain that covered well the full diversity and complexity of the SH3 domains encoded by the human genome. Hck SH3 domain was included in the study due to our earlier experience in engineering of its the binding specificity (Hiipakka & Saksela, 2007), while Fyn SH3 was included as it has been successfully used as a targeting scaffold by others (Grabulovski et al, 2007; Brack et al, 2014; Schlatter et al, 2015).

For construction of drHck-SH3, drAmphiphysin-SH3, drRBP3/III-SH3, drIRTKS-SH3, drSNX33-SH3, drEps8L1-SH3, drFISH/V-SH3, draCMS/I-SH3, drOSTF1-SH3, drFyn-SH3, drNPHP1-SH3, and drTec-SH3 libraries, RT and n-Src loop regions were randomized using the oligonucleotide-directed mutagenesis technique and NNK degenerate codons. To facilitate comparison of our study with the published work on Fyn-SH3, the general design of the strategy to randomize the the RT and n-Src loops in these SH3 domains was chosen to be the same as reported earlier by Grabulovski et al (2007). High-efficiency electroporation to E. coli SS320 host (Tonikian et al, 2007) resulted in libraries containing a total of 0.5-1.1×10$^{10}$ transformants, in which six positions in both the RT- and n-Src-loops were mutated. The quality of the libraries was assessed by DNA sequencing, and the proportion of clones containing planned random mutations in both loops were confirmed to be over 80% in all cases.

Performance Evaluation of drSH3 Phage Libraries

To assess the efficiency of each library scaffold to produce target specific drSH3 binders, phage display selections were performed using a panel of diagnostically or therapeutically relevant proteins as targets. (Dengue-2 virus NS1, Malaria HRP-II, CTLA-4, Her2, and HSA). Five rounds of affinity selections were performed on target proteins immobilized in immunotubes using an equal quantity of input of each infectious library phage. A successful selection generates increasingly more specific phage clones to the target protein with each round. This progress was monitored both by calculating the enrichment ratio: the number of phage bound to an immunotube coated with target protein divided by the number of phage bound to an uncoated control tube, as well as by phage-ELISA. Similar to the enrichment ratio, the phage-ELISA readout reflects the affinity and the number of phages displaying drSH3 domains that are specific to the target protein under investigation.

When using the drNPHP1-SH3 and drTec-SH3 phage libraries robust enrichment of binding to all five target proteins (NS1, HRP-II, CTLA-4, Her2, and HSA) could be observed, with the enrichment profile typically peaking after the third round of panning. By contrast, the progression of enrichment was considerably slower or not evident at all with the other drSH3-libraries. This is exemplified by FIG. 1, which shows enrichment of phage-ELISA reactivity against Dengue-2 virus NS1 protein during panning rounds 1-5 of the different drSH3 libraries.

In agreement with the robust enrichment of NS1 reactivity in the affinity-selected phage populations, sequencing of drNPHP1-SH3 and drTec-SH3 clones from the 5th round of panning against NS1 revealed the predominance of only 1-2 different clones, which are shown below. The novel sequences selected among the randomized loop residues are underlined.

NPHP1-drSH3 #1:
(SEQ ID NO: 16)
EEYIAVGDF<u>CTYTGPD</u>LTFKKGEILLVIE<u>RPFAHT</u>DGWWIAKDAKGNEGL
VPRTYLEPYS

NPHP1-drSH3 #2:
(SEQ ID NO: 17)
EEYIAVGDF<u>QPSMPCD</u>LTFKKGEILLVIE<u>QLQMCL</u>DGWWIAKDAKGNEGL
VPRTYLEPYS

Tec-drSH3 #1:
(SEQ ID NO: 18)
EIVVAMYDF<u>MSNSVHD</u>LRLERGQEYLILE<u>KQDKRG</u>VHWWRARDKYGNEGY
IPSNYVTGKK

Figure 2:
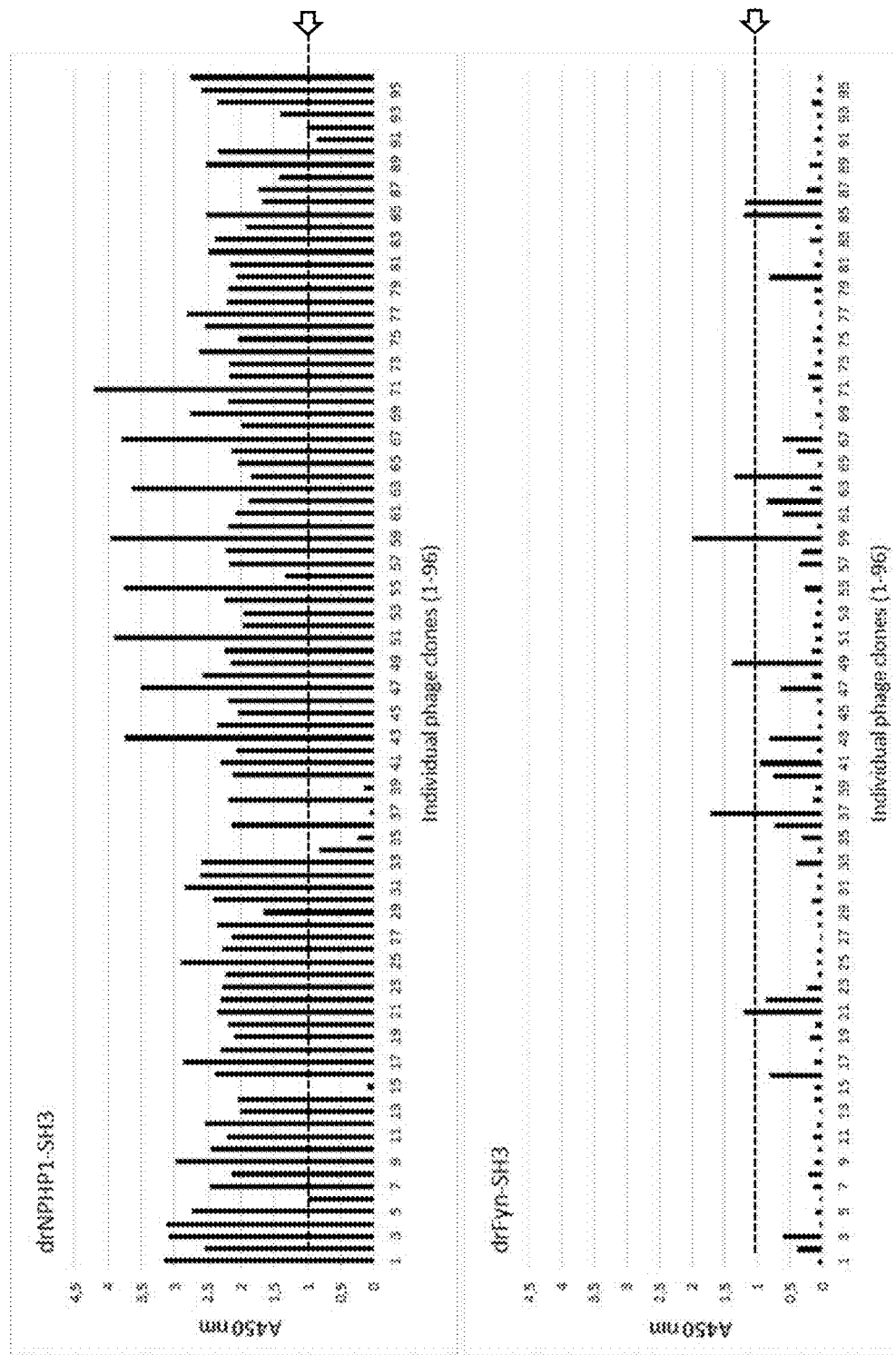
FIG. 2. Comparison of the capacity of drNPHP1-SH3 and drFyn-SH3 phage display libraries to generate individual clones showing reactivity against the NS1 antigen of Dengue-2 virus after four rounds of affinity panning. A total of 96 individual clones randomly picked from the 4th panning round were examined in both cases. Clones giving a readout ≥1 (A450 nm) in phage-ELISA were considered as promising NS1 binders (dashed line indicated by the arrow).

To examine the performance of the drSH3 libraries in another way, we also used phage-ELISA to compare the NS1 binding capacity of 96 individual phage clones randomly picked after four rounds of affinity panning of drNPHP1-SH3 and drFyn-SH3 libraries. As shown in FIG. 2, almost all drNPHP1-SH3 clones already showed strong binding at panning round 4, whereas only a few drFyn-SH3 clones showing modest reactivity could be observed, and none with the intense binding that was characteristic to the drNPHP1-SH3 clones.

In the next experiment we compared the 12 different drSH3 libraries in a competitive manner by combining them together in matching infectious titers to generate a large pooled library that was then used for an affinity panning experiment against NS1, HRP-II, Her2, and CTLA-4. After five rounds of affinity panning the SH3 backbone of 24 individual clones showing binding intensity ≥1 (A450 nm) in phage-ELISA against their cognate proteins was determined by DNA sequencing. Strikingly, all sequenced drSH3 clones were based on the Tec or the NPHP1 SH3 domain scaffold, as follows:

| Target | drSH3 scaffold | | |
| --- | --- | --- | --- |
| | NPHP1 | Tec | Others |
| NS1 | 58% | 42% | 0% |
| HRP-II | 71% | 29% | 0% |
| CTLA-4 | 96% | 4% | 0% |
| Her2 | 87% | 13% | 0% |

To test the suitability of other RT and n-Src loop randomization strategies for engineering of the NPHP1 and Tec SH3 scaffolds several additional large (typically >1×10$^{10}$) drNPHP1-SH3 and drTec-SH3 libraries were constructed (Table 2). Many of these showed similar or possibly even higher targeting capacity than the original libraries constructed according to the generic strategy shown in Table 1. For example, when the different drNPHP1-SH3 and drTec-SH3 libraries were tested as mixed pools in a competitive manner, after five round of affinity panning against NS1 the dominant clones in both cases represented a design where the RT-loop region contained a 6-residue substitution whereas the n-src loop contained a 6-residue insertion. The sequences of these clones are shown below with the novel sequences selected among the randomized loop residues (underlined) and the n-src loop residues shared by the insertion strategy (unlike in the strategy shown in Table 1) indicated in bold.

NPHP1-drSH3 #3:
(SEQ ID NO: 19)
EEYIAVGDF<u>YGCDPV</u>DLTFKKGEILLVIEKK<u>PSFVWI</u>PDGWWIAKDAKGN
EGLVPRTYLEPYS

-continued

Tec-drSH3 #2:
(SEQ ID NO: 20)
EIVVAMYDF<u>NTSSWW</u>DLRLERGQEYLILE<u>KN</u>SSFKFHDVHWWRARDKYGN
EGYIPSNYVTGKK

Tec-drSH3 #3:
(SEQ ID NO: 21)
EIVVAMYDF<u>HSTPWW</u>DLRLERGQEYLILE<u>KN</u>SSFTLWDVHWWRARDKYGN
EGYIPSNYVTGKK

In summary, we conclude that the human NPHP1 and Tec SH3 domains are superior scaffolds for construction of drSH3 libraries to be used for affinity selection of specific binder proteins against diverse target proteins of interest, when compared to similar libraries based on a representative panel of 10 other human SH3 domains, including Fyn SH3. The excellent performance of NPHP1 and Tec SH3 domains as affinity protein scaffolds can be achieved by different strategies used for randomization of the target binding loops. Whether one of these strategies provides a consistent advantage over the others is a question that will require further studies, but can be hypothesized to be a matter that may depend on the particular molecule used as the target.

TABLE 1

Randomization strategies for drSH3 libraries (SEQ ID NOS: 1-12).

|  | β1 | RT-loop | β2 | n-src-loop | β3 | distal loop | β4 | β5 |
|---|---|---|---|---|---|---|---|---|
| NPHP1 | EEYIAVGDF | --TAQQVG----- | DLTFKKGEILLVIE | -----KKPDGWWIAKDAK | ---------GNEGLVPRTYLEPYS | | | |
| Tec | EIVVAMYDF | --QAAEGH----- | DLRLERGQEYLILE | -----KNDVHWWRARDKY | ---------GNEGYIPSNYVTGKK | | | |
| Fyn | TLFVALYDY | --EARTED----- | DLSFHKGEKFQIL | -----NSSEGDWWEARSLTT | --------GETGYIPSNYVAPVD | | | |
| Hck | IIVVALYDY | --EAIHHE----- | DLSFQKGDQMVVL | ------EESGEWWKARSLAT | --------RKEGYIPSNYVARVD | | | |
| Amph | YKVETLHDF | --EAANSD----- | ELTLQRGDVVLVVPSDSEADQDAGWLVGVKESDWLQYRDLATYKGLFPENFTRRLD | | | | | |
| RIMBP#3 | KIMIAALDYDPGDGQMGGQGKGRLALRAGDVVMVYGP | ----MDDQGFYYGELG | ----------GHRGLVPAHLLDHMS | | | | | |
| IRTKS | QKVKTIFPH | --TAGSNKT---- | LLSFAQGDVITLL | ----IPEEKDGWLYGEHDVS | --------KARGWFPSSYTKLLE | | | |
| SNX33 | LKGRALYDF | --HSENKE----- | EISIQQDEDLVIFS | ----ETSLDGWLQGQNSR | ---------GETGLFPASYVEIVR | | | |
| Eps8L1 | KWVLCNYDF | --QARNSS----- | ELSVKQRDVLEVLD | ------DSRKWWKVRDPA | ---------GQEGYVPYNILTPYP | | | |
| FISH#5 | DVYVSIADY | --EGDEE------ | TAGFQEGVSMEVLE | -----RNPNGWWYCQILDGVK | ------PFKGWVPSNYLEKKN | | | |
| CMS#1 | VDYIVEYDY | --DAVHDD----- | ELTIRVGEIIRNVK | ----KLQEEGWLEGELN | ---------GRRGMFPDNFVKEIK | | | |
| OSTF1 | KVFRALYTF | --EPRTPD----- | ELYFEEGDIIYITD | -----MSDTNWWKGTSK | ----------GRTGLIPSNYVAEQA | | | |

Residues substituted by six random amino acids (XXXXXX) in both RT and n-Src-loops are highlighted in grey.
Beta-strands (β1-β5) shared by each SH3 domain are shown in bold, and conserved amino acid residues are underlined.

TABLE 2

Randomization strategies for NPHP1-SH3 (SEQ ID NO: 1) and Tec-SH3 (SEQ ID NO: 2) libraries. RT and n-Src-loops are shown in bold. Random amino acids in both RT and n-Src-loops are shown as X. Eight consecutive randomized amino acids are marked as XX(6)X.

| NPHP1-SH3 | EEYIAVGDFTAQQVGDLTFKKGEILLVIEKK------PDGWWIAKDAKGNEGLVPRTYLEPYS |
|---|---|
| NET-drNPHP1-SH3 | XXXXXX XXXXXX- |
| NBT-drNPHP1-SH3 (II) | XXXXXX XXXXXX |
| NBT-drNPHP1-SH3 (III) | XX(6)X XXXXXX |
| NET-drNPHP1-SH3 (IV) | XXXXXX XX(6)X |
| NET-drNPHP1-SH3 (V) | XX(6)X XX(6)X |
| NET-drNPHP1-SH3 (VI) | XXXXXX -XX(6)X- |
| | |
| Tec-SH3 | EIVVAMYDF--QAAEGHLRLERGQEYLILEKN------DVHWWRARDKYGNEGYIPSNYVTGKK |
| NET-drTec-SH3 | XXXXXX --XXXXXX- |
| NBT-drTec-SH3 (II) | XXXXXX XXXXXX |
| NBT-drTec-SH3 (IIb) | XXXXXX XXXXXX- |
| NET-drTec-SH3 (II)-PP | PPXXXXXX XXXXXX |
| NET-drTec-SH3 (III) | XX(6)X XXXXXX |
| NBT-drTec-SH3 (IV) | XXXXXX XX(6)X |
| NBT-drTec-3H3 (V) | XX(6)X XX(6)X |
| NBT-drTec-SH3 (VI) | XXXXXX -XX(6)X- |

REFERENCES

Amako, Y., Igloi, Z., Mankouri, J., Kazlauskas, A., Saksela, K., Dallas, M., Peers, C., Harris, M., 2013. Hepatitis C virus NS5A inhibits mixed lineage kinase 3 to block apoptosis. J Biol Chem 288, 24753-24763.

Antoku, S., Saksela, K., Rivera, G. M., Mayer, B. J., 2008. A crucial role in cell spreading for the interaction of Abl PxxP motifs with Crk and Nck adaptors. J Cell Sci 121, 3071-3082.

Asbach, B., Ludwig, C., Saksela, K., Wagner, R., 2012. Comprehensive analysis of interactions between the Src-associated protein in mitosis of 68 kDa and the human Src-homology 3 proteome. PLoS One 7, e38540.

Binz, H. K., Pluckthun, A., 2005. Engineered proteins as specific binding reagents. Current opinion in biotechnology 16, 459-469.

Brack, S., Attinger-Toller, I., Schade, B., Mourlane, F., Klupsch, K., Woods, R., Hachemi, H., von der Bey, U., Koenig-Friedrich, S., Bertschinger, J., Grabulovski, D., 2014, A bispecific HER2-targeting FynomAb with superior antitumor activity and novel mode of action. Molecular cancer therapeutics 13, 2030-2039.

Ebsen, H., Lettau, M., Kabelitz, D., Janssen, O., 2014. Identification of SH3 domain proteins interacting with the cytoplasmic tail of the a disintegrin and metalloprotease 10 (ADAM10). PLoS One 9, e102899.

Fellouse, F. A. & Pal, G. 2005, Methods for the construction of phage-displayed libraries, in Phage Display in Biotechnology and Drug Discovery Vol. 3 (ed. Sidhu, S. S.) Taylor and Francis Group, Boca Raton, Fla., pp. 111-142.

Gebauer, M., Skerra, A., 2009. Engineered protein scaffolds as next-generation antibody therapeutics. Current opinion in chemical biology 13, 245-255.

Grabulovski, D., Kaspar, M., Neri, D., 2007. A novel, non-immunogenic Fyn SH3-derived binding protein with tumor vascular targeting properties. J Biol Chem 282, 3196-3204.

Heikkinen, L. S., Kazlauskas, A., Melen, K., Wagner, R., Ziegler, T., Julkunen, I., Saksela, K., 2008. Avian and 1918 Spanish influenza a virus NS1 proteins bind to Crk/CrkL Src homology 3 domains to activate host cell signaling. J Biol Chem 283, 5719-5727.

Hey, T., Fiedler, E., Rudolph, R., Fiedler, M., 2005. Artificial, non-antibody binding proteins for pharmaceutical and industrial applications. Trends in biotechnology 23, 514-522.

Hiipakka, M., Poikonen, K., Saksela, K., 1999. SH3 domains with high affinity and engineered ligand specificities targeted to HIV-1 Nef. J Mol Biol 293, 1097-1106.

Hiipakka, M., Saksela, K., 2007. Versatile retargeting of SH3 domain binding by modification of non-conserved loop residues. FEBS Lett 581, 1735-1741.

Igloi, Z., Kazlauskas, A., Saksela, K., Macdonald, A., Mankouri, J., Harris, M., 2015. The hepatitis C virus NS5A protein blocks EGFR degradation via a proline motif dependent interaction. J Gen Virol.

Järviluoma, A., Strandin, T., Lulf, S., Bouchet, J., Mäkelä, A. R., Geyer, M., Benichou, S., Saksela, K., 2012. High-affinity target binding engineered via fusion of a single-domain antibody fragment with a ligand-tailored SH3 domain. PLoS One 7, e40331.

Kesti, T., Ruppelt, A., Wang, J. H., Liss, M., Wagner, R., Tasken, K., Saksela, K., 2007. Reciprocal regulation of SH3 and SH2 domain binding via tyrosine phosphorylation of a common site in CD3epsilon. J Immunol 179, 878-885.

Kleino, I., Järviluoma, A., Hepojoki, J., Huovila, A. P., Saksela, K., 2015. Preferred SH3 domain partners of ADAM metalloproteases include shared and ADAM-specific SH3 interactions. PLoS One 10, e0121301.

Kleino, I., Ortiz, R. M., Yritys, M., Huovila, A. P., Saksela, K., 2009. Alternative splicing of ADAM15 regulates its interactions with cellular SH3 proteins. J Cell Biochem 108, 877-885.

Kunkel, T. A., Roberts, J. D. & Zakour, R. A., 1987. Rapid and efficient site-specific mutagenesis without phenotypic selection. Methods Enzymol. 154, 367-382.

Karkkäinen, S., Hiipakka, M., Wang, J. H., Kleino, I., Vähä-Jaakkola, M., Renkema, G. H., Liss, M., Wagner, R., Saksela, K., 2006. Identification of preferred protein interactions by phage-display of the human Src homology-3 proteome. EMBO Rep 7, 186-191.

Li, S. S., 2005. Specificity and versatility of SH3 and other proline-recognition domains: structural basis and implications for cellular signal transduction. Biochem J 390, 641-653.

Macias, M. J., Wiesner, S., Sudol, M., 2002. WW and SH3 domains, two different scaffolds to recognize proline-rich ligands. FEBS Lett 513, 30-37.

Mayer, B. J., 2001. SH3 domains: complexity in moderation. J Cell Sci 114, 1253-1263.

Mayer, B. J., and Saksela, K., 2005. SH3 domains, in: Cesareni, G., Gimona, M., Sudol, M., and Yaffe, M. (Ed.), Modular Protein Domains. Wiley-VCH, Weinheim, pp. 37-58.

Neuvonen, M., Kazlauskas, Martikainen, M., Hinkkanen, A., Ahola, T., Saksela, K., 2011. SH3 domain-mediated recruitment of host cell amphiphysins by alphavirus nsP3 promotes viral RNA replication. PLoS Pathog 7, e1002383.

Panni, S., Dente, L., Cesareni, G., 2002. In vitro evolution of recognition specificity mediated by SH3 domains reveals target recognition rules. J Biol Chem 277, 21666-21674.

Petrenko, V. A. & Smith, G. P., 2005. Vectors and modes of display. in Phage Display in Biotechnology and Drug Discovery Vol. 3 (ed. Sidhu, S. S.) Taylor and Francis Group, Boca Raton, Fla., pp. 63-110.

Pietrek, M., Brinkmann, M. M., Glowacka, I., Enlund, A., Havemeier, A., Dittrich-Breiholz, O., Kracht, M., Lewitzky, M., Saksela, K., Feller, S. M., Schulz, T. F., 2010. Role of the Kaposi's sarcoma-associated herpesvirus K15 SH3 binding site in inflammatory signaling and B-cell activation. J Virol 84, 8231-8240.

Saksela, K., Permi, P., 2012. SH3 domain ligand binding: What's the consensus and where's the specificity? FEBS Lett 586, 2609-2614.

Schlatter, D., Brack, S., Banner, D. W., Batey, S., Benz, J., Bertschinger, J., Hiker, W., Joseph, C., Rufer, A., van der Klooster, A., Weber, M., Grabulovski, D., Hennig, M., 2012. Generation, characterization and structural data of chymase binding proteins based on the human Fyn kinase SH3 domain. mAbs 4, 497-508.

Schmaier, A. A., Zou, Z., Kazlauskas, A., Emert-Sedlak, L., Fong, K. P., Neeves, K. B., Maloney, S. F., Diamond, S L., Kunapuli, S. P., Ware J., Brass, L. F., Smithgall, T. E., Saksela, K., Kahn, M. L., 2009. Molecular priming of Lyn by GPVI enables an immune receptor to adopt a hemostatic role. Proc Natl Acad Sci USA 106, 21167-21172.

Sicheri, F., Kuriyan, J., 1997. Structures of Src-family tyrosine kinases. Current opinion in structural biology 7, 777-785.

Sidhu, S. S., Lowman, H. B., Cunningham, B. C. & Wells, J. A., 2000. Phage display for selection of novel binding peptides. Methods Enzymol. 328, 333-363.

Thompson, O., Kleino, I., Crimaldi, L., Gimona, M., Saksela, K., Winder, S. J., 2008. Dystroglycan, Tks5 and Src mediated assembly of podosomes in myoblasts. PLoS One 3, e3638.

Thompson, O., Moore, C. J., Hussain, S. A., Kleino, L., Peckham, M., Hohenester, E., Ayscough, K. R., Saksela, K., Winder, S. J., 2010. Modulation of cell spreading and cell-substrate adhesion dynamics by dystroglycan. J Cell Sci 123, 118-127.

Tonikian R., Xhang, Y., Boone, C., Sidhu, S. S., 2007. Identifying specificity profiles for peptide recognition modules from phage-displayed peptide libraries. Nature Protocols 2, 1368-1386.

Vingadassalom, D., Kazlauskas, A., Skehan, B., Cheng, H. C., Magoun, L., Robbins, D., Rosen, M. K., Saksela, K., Leong, J. M., 2009, Insulin receptor tyrosine kinase substrate links the *E. coli* 0157:1-H7 actin assembly effectors Tir and EspF(U) during pedestal formation. Proc Natl Acad Sci USA 106, 6754-6759.

Viti, F., Nilsson, F., Demartis, S., Huber, A., and Neri, D., 200. Design and use of phage display libraries for the selection of antibodies and enzymes. Methods Enzymol 326, 480-505.

Voss, M., Lettau, M., Janssen, O., 2009. Identification of SH3 domain interaction partners of human FasL (CD178) by phage display screening. BMC immunology 10, 53.

Weidle, U. H., Auer, J., Brinkmann, U., Georges, G., Tiefenthaler, G., 2013. The emerging role of new protein scaffold-based agents for treatment of cancer. Cancer genomics & proteomics 10, 155-168.

The invention claimed is:

1. A recombinant binding protein having a specific Src homology 3 (SH3) domain based binding affinity to a target molecule, said binding protein comprising a nephrocystin (NPHP1) derived SH3 domain, wherein
   a) at least two amino acids are substituted in the RT-loop of said SH3 domain or added to the RT-loop, and/or
   b) at least two amino acids are substituted in the n-src-loop of said SH3 domain or added to the n-src-loop,
   and wherein said nephrocystin (NPHP1) derived SH3 domain has an amino acid sequence having at least 85% sequence identity to the amino acid sequence of SEQ ID NO:1 outside the RT-loop and n-src-loop, wherein said RT loop corresponds to amino acid positions 8-17 of SEQ ID NO:1, and wherein said n-src-loop corresponds to amino acid positions 28-34 of SEQ ID NO:1.

2. The binding protein according to claim 1, wherein said nephrocystin (NPHP1) derived SH3 domain has an amino acid sequence having at least 90% sequence identity to the amino acid sequence of SEQ ID NO:1 excluding amino acid positions corresponding to the RT-loop and n-src-loop.

3. The binding protein according to claim 1, wherein at least one amino acid in the RT-loop is deleted.

4. The binding protein according to claim 1, wherein at least one amino acid in the n-src-loop is deleted.

5. A method for the production of a library comprising recombinant derivatives of the SH3 domain of nephrocystin (NPHP1) having the sequence of SEQ ID NO: 1, said method comprising the steps of
   (a) generating recombinant derivatives of the SH3 domain of NPHP1 of SEQ ID NO: 1 by substituting or adding at least two amino acids in the RT loop of said SH3 domain, and/or substituting or adding at least two amino acids in the n-src-loop of said SH3 domain, and
   (b) building a library comprising the recombinant derivatives of the SH3 domain generated in step (a);
   wherein the recombinant derivatives of the SH3 domain of NPHP1 retain at least 85% identity to the amino acid of SEQ ID NO: 1 outside the RT and n-src loops; and wherein the RT loop is located at amino acid positions 8-17 of SEQ ID NO: 1, and the n-src loop is located at amino acid positions 28-34 of SEQ ID NO: 1.

6. The method according to claim 5, wherein said NPHP1 derived SH3 domain has an amino acid sequence having at least 90% sequence identity to the amino acid sequence of SEQ ID NO:1 excluding amino acid positions corresponding to the RT-loop and n-src-loop.

7. The method according to claim 5, wherein the library built in step (b) is a phage display library.

8. The method according to claim 5, wherein in step (a) six amino acids in the RT loop are randomly substituted, and four amino acids in the n-src loop are randomly substituted and two random amino acids are added to the n-src loop.

9. The method according to claim 5 further comprising steps for selecting from the library comprising recombinant derivatives of the SH3 domain of NPHP1, said steps for selecting from the library comprising the steps of (a) contacting the library comprising derivatives of the SH3 domain of NPHP1 with a target molecule under conditions and for a time sufficient to permit the derivatives and the target molecule to interact, wherein the target molecule is not a natural NPHP1 SH3 binding ligand; and (b) selecting from the library one or more derivatives of the SH3 domain of nephrocystin (NPHP1) having a specific binding affinity to the target molecule, wherein the selected derivatives of the SH3 domain of NPHP1 retain at least 85% identity to the amino acid of SEQ ID NO: 1 outside the RT and n-src loops; and wherein the RT loop is located at amino acid positions 8-17 of SEQ ID NO: 1, and the n-src loop is located at amino acid positions 28-34 of SEQ ID NO: 1.

10. The method according to claim 9, wherein said target molecule is a protein or peptide.

11. A library obtained by a method for the production of a library comprising recombinant derivatives of the SH3 domain of nephrocystin (NPHP1) having the sequence of SEQ ID NO: 1, said method comprising the steps of
   (a) generating recombinant derivatives of the SH3 domain of NPHP1 of SEQ ID NO: 1 by substituting or adding at least two amino acids in the RT loop of said SH3 domain, and/or substituting or adding at least two amino acids in the n-src-loop of said SH3 domain, and
   (b) building a library comprising the recombinant derivatives of the SH3 domain generated in step (a);
   wherein the recombinant derivatives of the SH3 domain of NPHP1 retain at least 85% identity to the amino acid of SEQ ID NO: 1 outside the RT and n-src loops; and wherein the RT loop is located at amino acid positions 8-17 of SEQ ID NO: 1, and the n-src loop is located at amino acid positions 28-34 of SEQ ID NO: 1.

* * * * *